United States Patent [19]
Karpf et al.

[11] Patent Number: 5,217,875
[45] Date of Patent: Jun. 8, 1993

[54] METHOD FOR DETECTING BIOLOGICAL ACTIVITIES IN A SPECIMEN AND A DEVICE FOR IMPLEMENTING THE METHOD

[75] Inventors: Hellfried Karpf, Graz, Austria; Herbert Smole, Diessenhofen, Switzerland

[73] Assignee: AVL AG, Switzerland

[21] Appl. No.: 474,786

[22] PCT Filed: Nov. 24, 1989

[86] PCT No.: PCT/AT89/00110
§ 371 Date: Mar. 29, 1990
§ 102(e) Date: Mar. 29, 1990

[87] PCT Pub. No.: WO90/13663
PCT Pub. Date: Nov. 15, 1990

[30] Foreign Application Priority Data

May 12, 1989 [AT] Austria .................................. 1147/89

[51] Int. Cl.$^5$ .................... C12Q 1/02; C12M 1/34; G06K 9/00
[52] U.S. Cl. ..................... 435/34; 435/291; 435/817; 382/6
[58] Field of Search ............ 435/34, 291, 817; 436/800; 382/6

[56] References Cited

U.S. PATENT DOCUMENTS

Re. 31,879  5/1985  Lübbers ............................. 436/133
4,495,293  1/1985  Shaffar .............................. 436/172

FOREIGN PATENT DOCUMENTS 0333253   9/1989  European Pat. Off.
57-207861 12/1982  Japan.
82/04264   8/1982  PCT Int'l Appl.

OTHER PUBLICATIONS

MacFaddin, J. F., "Urease Test", Biochemical Tests for Identification of Medical Bacteria, The Williams & Wilkins Company, 1976, pp. 187-194.
MacFaddin, J. F., "Klinger's Iron Agar/Triple Sugar Iron Agar Tests", Biochemical Tests for Identification of Medical Bacteria, The Williams & Wilkins Company, 1976, pp. 108-118.

Primary Examiner—Michael G. Wityshyn
Assistant Examiner—Jane A. Williams
Attorney, Agent, or Firm—Hill, Steadman & Simpson

[57] ABSTRACT

A method for detecting biological activities in a specimen, for instance a blood sample, employing a sealable container with a culture medium, into which the sample is introduced, wherein metabolic processes are enhanced in the presence of microorganisms in the sample, thereby causing changes to take place in the concentrations of the substances subject to such processes. The concentration changes are measured by optodes that are in direct contact with the sample, and by an excitation and detection assembly assigned to these optodes, to which is connected an evaluation unit for determining concentration changes of the substances over time.

15 Claims, 5 Drawing Sheets

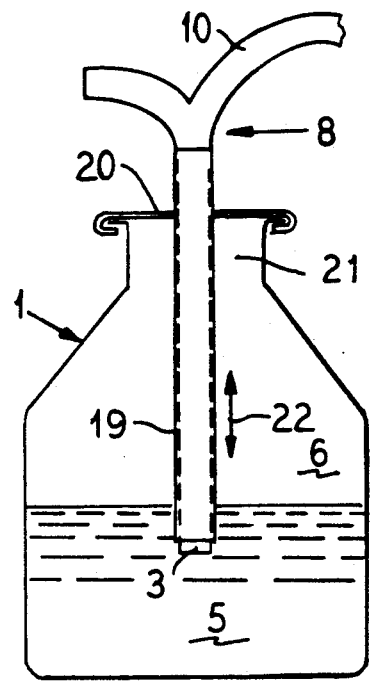
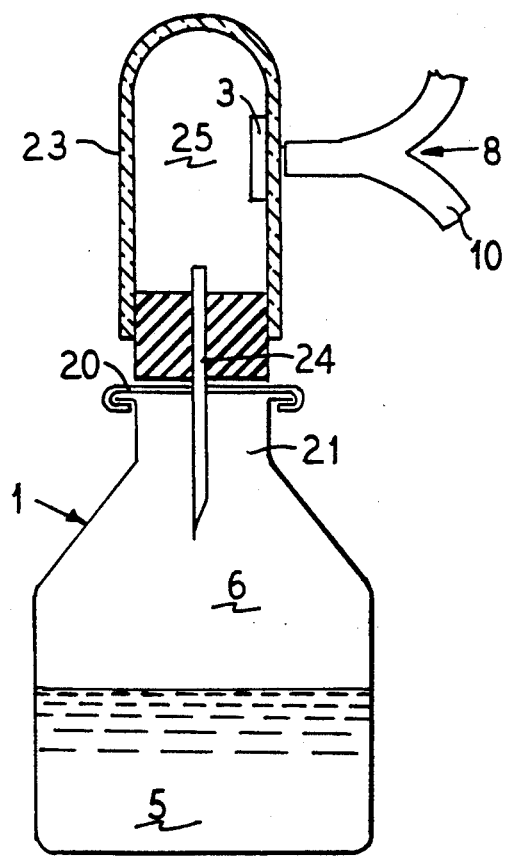
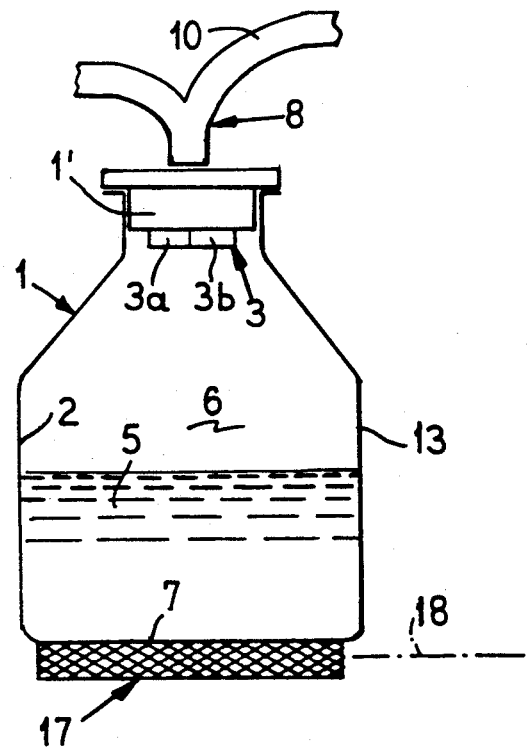

METHOD FOR DETECTING BIOLOGICAL ACTIVITIES IN A SPECIMEN AND A DEVICE FOR IMPLEMENTING THE METHOD

BACKGROUND OF THE INVENTION

1. Field of the Invention

This invention relates to a method for detecting biological activities in a specimen, where the specimen and a culture medium are filled into a sealable container and are exposed to conditions enabling metabolic processes to take place in the presence of microorganisms in the sample, the concentration of initial substances being lowered and that of metabolic products being raised, and to a device for implementation of this method.

2. Description of the Prior Art

In many applications it must be possible to determine quickly whether a specimen is contaminated by microorganisms, such as bacteria, in particular in medical applications, in the pharmaceutical industry, food industry, or in environmental protection activities. The term "specimen" has a most comprehensive meaning here, including substances such as solid and liquid biological material (e.g., blood), food samples, such as frozen foods and preserved or canned foods, packaging material, clinical instruments and laboratory equipment, or samples taken from their surfaces, medical apparatus, first-aid and dressing material, soil and water samples, especially samples of drinking water.

For a long time, purely manual methods have been used in which the specimen to be assessed is put into a culture bottle containing a culture medium, and the growth of the culture is inspected only visually at given time intervals, and the type or presence of a microorganism is inferred from this observation.

In addition, some technical procedures and devices are known, with which the biological activities in a sample caused by microorganisms may be determined, and where the $CO_2$ produced by the metabolism of the microorganism, or rather, the change in $CO_2$ content, is employed as a measurement for determining the biological activity.

It is a known procedure, for instance, to bottle the sample to be assessed together with a radioactively labelled liquid culture medium and to test the atmosphere over the culture medium for radioactive gases, following which the presence of microorganisms in the simple may be determined.

Measuring systems of this kind are described in U.S. Pat. Nos. 3,676,679 and 3,935,073, for example. Although such systems are quick and reliable, they have certain disadvantages, i.e., radioactive substances must be handled and samples must repeatedly be taken from the gas space above the culture medium for continuous monitoring. When the samples are removed from the gas space, the remaining samples to be monitored may easily be contaminated by the sample-taking element and measuring errors may occur.

In European application 0 158 497 a system is disclosed in which the biological activity of a specimen is determined by means of infrared absorption. In this method a specimen is introduced into a sealable vessel containing a liquid culture medium, and is tested for the presence of microorganisms. The vessel is subjected to specific conditions, i.e., certain temperatures are maintained over given periods of time, thus enhancing the metabolism of the microorganisms, during which process $CO_2$ is produced in the gas space above the culture medium by conversion of the carbon source. A sample is taken from the gas space and introduced into a measuring cell, and the $CO_2$ content is measured by infrared absorption. Again, the subsequent samples may be contaminated, and another drawback is that infrared absorption is a less sensitive manner of measuring than radioactive labelling.

In order to avoid the problem of cross-contamination, the European application 0 104 463 proposes a method as well as a device of the kind mentioned in the introduction, which also are based on the detection of $CO_2$—produced by metabolic processes—by way of infrared absorption. In this method no sample is taken, but infrared radiation is directly transmitted through the wall of the vessel into the gas space above the culture medium, and its absorption is determined. Due to this non-invasive measuring method cross-contaminations are largely eliminated; the disadvantage of this method, however, is its lack of sensitivity compared to radiometric methods, as well as the fact that the measurement is distorted by other gas components absorbing radiation in the same frequency band as $CO_2$. A suitable example are the absorption bands of hydrogen vapor. The sample vessels employed must be permeable within a relatively narrow frequency range, which will only permit the use of specific materials for these vessels. An additional disadvantage is that the generation and filtering of the required infrared radiation is comparatively complex and expensive.

SUMMARY OF THE INVENTION

It is an object of this invention to propose a method and device for detecting biological activities in a specimen, which has at least the same sensitivity as radiometric methods, and which offers the user a simple and inexpensive technique providing him with detailed information on the type of microorganisms while eliminating the danger of cross-contamination.

According to the present invention this object is achieved by continuously measuring the concentration of at least one (produced or consumed) substance subject to conversion by metabolic processes, and by measuring the change in concentration of at least one other substance in case of a concentration change in the first substance by a given threshold value. A test signal is generated by optodes in direct contact with the substances to be assessed, and the change over time of this signal serve as indicators for the presence of microorganisms. The optical sensors or optodes, which may be mass-produced cheaply and which are in direct contact with the substance to be assessed, permit continuous monitoring in closed systems. New optodes are used for each sample, such that cross-contaminations are eliminated. In the simplest variant, for instance, a bisensor may suffice to determine the type of microorganisms by sensing the changes in substance concentrations relative to the initial concentrations.

The invention provides that concentrations be measured of at least two substances from the group of $CO_2$, $O_2$, $H^+(pH)$, $NH_4^+$, $H_2S$, $H_2$, the indicator medium of the optodes responding to a change in substance concentrations by changing its luminescence, absorption or reflectance behavior, or that concentrations be measured of at least two substances from the group of $CO_2$, $O_2$, $H^+(pH)$, $NH_4^+$, $H_2S$, $H_2$, here the indicator medium of the optodes responding to a change in substance concentrations by changing the luminescence decay time of the luminescent radiation emitted. In this way all substances playing a major role in metabolic processes can be detected by at least one optical measuring system.

In particular, the invention provides—for instance, for the testing of blood samples—that the $CO_2$ concentration be measured continuously and that the changes in $O_2$ concentration and pH be determined upon a rise of the $CO_2$ concentration by 0.1 to 10% above a given minimum.

The invention will also permit continuous measuring of the $O_2$ concentration and determination of the changes in $CO_2$ concentration and pH upon a drop of the $O_2$ concentration by 0.1 to 10% below a given maximum. The advantage of this variant is that significant changes in the $O_2$ concentration may be detected earlier.

In case of a change in $CO_2$ concentration by 0.1 to 10% the table below will assist in quickly detecting the relevant bacterial strains, or at least narrowing down the species to be considered to just a few.

| Group | O2-change | pH-change | Gram |
|---|---|---|---|
| Enterobacteriaceae | ↓ | ↓ | neg |
| Pseudomonas species | ↓↓ | +/−o | neg |
| Acinetobacter species | ↓↓ | ↓ | neg |
| Bacteroide species | +/−o | ↓ | neg |
| Staphylococcus | ↓↓ | ↓↓ | pos |
| *Staphylococcus epidermidis* | ↓ | ↓ | pos |
| *Streptococcus faecalis* | ↓↓ | ↓↓ | pos |
| *Streptococcus pyogenes* | ↓ | ↓↓ | pos |
| *Streptococcus pneumoniae* | ↓ | ↓↓ | pos |
| *Candida albicans* | ↓ | ↓↓ | pos |
| *Clostridium perfringens* | +/−o | ↓↓ | pos |

For the change in $O_2$ concentration, a slight decrease (↓) indicates a change of 3-21% of the initial or maximum value, whereas a sharp decrease (↓↓) indicates a change of more than 21%. As regards the pH change, the threshold between slight and sharp decreases is 0.15% of the initial value.

In the instance of a slight decrease in $O_2$ concentration and a slight decrease in pH (towards acid values) the presence of Enterobacteria or of *Staphylococcus epidermidis* may be assumed.

In addition, Gram staining of the sample may be determined by conventional means, negative Gram staining indicating Enterobacteria and positive Gram staining *Staphylococcus epidermidis*.

Due to the changes in $O_2$ concentration and pH given in the above table the indicated species may be distinguished.

For simple applications, or if the type of microorganism is known or determined by other procedures, the proposal is put forward that the $CO_2$ concentration be measured with the use of a $CO_2$— sensitive fluorescence sensor located in the container, which is provided with excitation radiation from an outside source, and that the change over time of the signal emitted by the fluorescence sensor be used to indicate the presence of microorganisms.

The invention also provides that a culture medium containing a carbon compound be filled into a sealable container, and that a fluorescent indicator be added to the culture medium, which indicator responds to the change in $CO_2$ content by a change in its fluorescence behavior, and that a blood sample be introduced into the container, which may be subject to metabolic processes in the presence of microorganisms, during which processes $CO_2$ is produced, and that the content of the container be exposed to excitation radiation and the radiation emitted by the fluorescent indicator be measured, a change in fluorescence behavior indicating the presence of microorganisms. For example, indicator capsules as disclosed in the German application 23 60 384 may be added, or rather, micro-capsules containing an indicator, whose walls are made from polymerized hydrophilic monomers, and which have a diameter of 20 to 200 nm.

According to the invention, a device for detecting biological activities in a specimen, comprising a sealable container containing a culture medium into which the sample is introduced, and further comprising structure enabling metabolic processes to take place in the presence of microorganisms in the sample, is characterized by the use of several optodes for simultaneous assessment of several substances whose concentrations are subject to changes by the metabolic processes, and by assigning an excitation and detection assembly to each optode, which in turn is connected with an evaluation unit determining the change over time of the substance concentrations. Combining two optodes (e.g., $O_2$ and pH) to form a bisensor, or three optodes (e.g., $CO_2$, $O_2$, pH) to form a tri-sensor may be of advantage.

According to the invention optodes are provided for selective detection of at least two substances from the group of $CO_2$, $O_2$, $H_2$, $H^+$(pH), $NH_4^+$ and $H_2S$, that are present during the metabolic process as initial, intermediate or final products.

The excitation and detection assembly may comprise a light source and a detector as well as, preferably, a two-armed optical waveguide transmitting excitation radiation to the optode or optodes and carrying the optical signal to the detector.

In a preferred variant of the invention the optodes are combined to form a multilayer sensor.

In a simple variant of the invention the optodes are attached to the inside of the wall of a transparent container and are connected to the evaluation unit via the excitation and detection assembly that may be placed flush against the outside of the wall of the container. The optodes, which may be mass-produced cheaply, are attached with an adhesive to the inner surface of the wall of the sample container, which is then filled with the culture medium, sealed and stored. After the addition of the specimen, for instance, a blood sample, the container is thermostat-controlled for the time required for the growth of the culture, and is shaken if necessary, whereupon the concentration of the substance subject to chemical reaction by the metabolic processes is measured, for example via an optical fiber waveguide attached to the outer surface of the wall of the container.

According to the invention it is possible to place at least the optodes in the gas space of the, at least partly transparent-container above the culture medium mixed with the sample, and to use these optodes for measuring the concentration of at least one gaseous metabolite.

It is provided in a further variant of the invention that the optodes be located on a transparent stopper used for sealing the container.

The method will also permit, however, to place the optodes in a part of the container covered by the culture medium mixed with the sample, possibly at the bottom of the container, and to use the same for measuring the concentration of at least one substance in the culture medium. With this arrangement the metabolite is measured immediately at the place where it is produced, which will permit more rapid assessment as to whether a culture is positive or negative.

According to a particularly favorable variant of the invention there is provided a device for temperature control of the sample, in which several containers are placed in respective labelled positions at the same time, each container being assigned an excitation and detection assembly transmitting excitation radiation to the optodes located in each container and detecting the ensuing optical signal, and the signals of the detection assembly are carried to the evaluation unit together with a position identification signal. The device used for temperature control may be configured as a temperature-controlled supporting rack of the chessboard type, which will permit a large number of culture bottles, e.g., up to 600, to be monitored simultaneously. As compared to conventional equipment of this kind, no further handling of the samples is required once they have been filled into their individual bottles, since both incubating process and continuous monitoring are fully automated in the device of the invention. Unlike conventional measuring techniques, in which the individual culture bottles must be inserted into an evaluation unit by hand once or twice daily, the technique of taking measurements continuously will allow the point in time when a culture becomes positive to be determined without delay. After this point has been reached other substances involved in the metabolic process may be assessed optically and the type of microorganisms may be determined. Thus a highly sensitive automatic measuring system permitting noninvasive, continuous measuring techniques is provided by the invention. The evaluation unit either includes a microcomputer indicating the status of each individual container, or it is connected to a computer via an interface.

In another variant of the invention provisions are made for a device for temperature control of the sample, which holds several containers at the same time, and for a feed mechanism or sample changer automatically taking the individual containers to a measuring station, in which the optodes located in each container enter into optical contact with the excitation and detection assembly. Whereas the variant described in the above paragraph has no movable parts at all, the variant of this paragraph has a conventional sample changer for automatically taking each sample to a measuring station. The advantage of this arrangement is that the electronic or electro-optical equipment need not be so elaborate.

According to the invention it is also possible to fasten the optodes at the tip of a probe to be inserted into the container, which probe contains lightguide elements from the excitation and detection assembly. The probe may be inserted through an opening sealed by a septum and introduced into the culture medium mixed with the sample or into the gas space thereabove.

A further variant of the invention provides that the container be sealed by a septum which may be punctured with the hollow needle of a sampling vessel (vacutainer), the optodes being located in the sampling vessel and a flow connection being established between the gas space of the container and the optodes via the hollow needle of the sampling vessel, after the sample has been added to the culture medium in the container. As a sampling vessel an evacuated vessel may be used, for example, to whose inner wall surface a $CO_2$ optode and an $O_2$ optode may be affixed. The sample, e.g. blood, is sucked into the container by the vacuum applied to the vessel. The septum of the container holding the culture medium is pierced with the needle and the blood is introduced into the culture bottle. Via the hollow needle $CO_2$ and $O_2$ are conveyed from the gas space above the culture medium to the sensor, where they are measured. Culture bottle and sampling vessel are preferably designed as one-way articles that are discarded after use.

BRIEF DESCRIPTION OF THE DRAWINGS

Following is a more detailed description of the invention as illustrated by the accompanying drawings, in which FIG. 1 gives a schematical view of a device of the invention, FIGS. 2a, 2b, 3, 4 give variants of the device in FIG. 1, FIG. 5 gives a variant for automated measuring of several containers at once, FIGS. 6 and 7 give variants of FIG. 5 in detail, and FIGS. 8 to 10 give measured curves.

DESCRIPTION OF THE PREFERRED EMBODIMENTS

Figure 1:
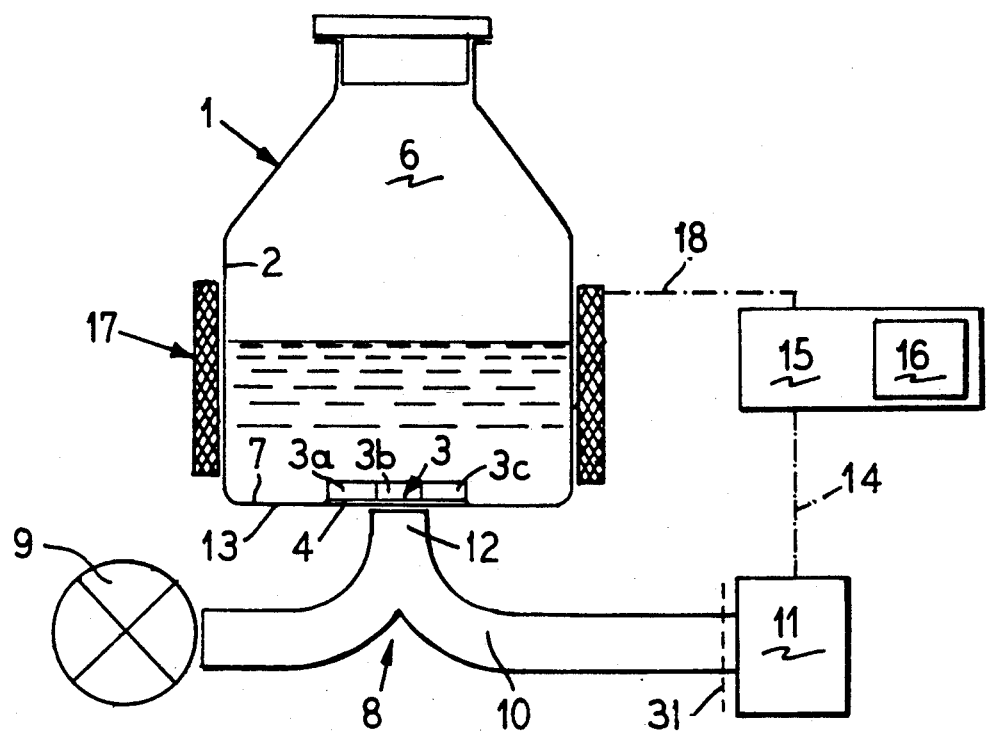

The device of FIG. 1 for detecting biological activities in a sample has a sealable, optically transparent container 1, with an optode 3 attached to the inner surface 2 of its wall, bonded by a transparent adhesive layer 4, for example.

Instead of a single optode 3 for a substance to be assessed, two or more optodes 3a, 3b and 3c may be combined into a multilayer sensor, which will permit simultaneous detection of the changes in $O_2$ and $CO_2$ concentrations and in pH, for example. The individual optodes 3a to 3c or their indicator media may be stacked in layers one above the other, or they may be embedded in a polymer membrane in homogeneous distribution. The combination of a $CO_2$ and an $O_2$ optode into a sensor is described in EP-A 105 870, for example.

Instead of the optode marked 3 in the variants discussed below, optodes may be provided for measuring $O_2$, $CO_2$, $H^+$(pH), $NH_4^+$, $H_2S$ and $H_2$, or rather, a specific combination of these optodes in accordance with the particular requirements.

Container 1 contains the culture medium 5 with one carbon compound (glucose), for instance, which is converted by metabolic processes of microorganisms in the sample into a metabolic product, for example $CO_2$, during which processes $O_2$ is being consumed and the pH is subject to change. As a consequence there are changes in the concentration of the metabolic product and the initial substances in the gas space 6 above the culture medium 5 and in the culture medium itself, which are detected by means of the optodes 3a, 3b and 3c placed at the bottom 7 of the container 1 in FIG. 1. The excitation and detection assembly 8 comprises a light source 9, a detector 11 and a two-armed lightguide 10, one of whose arms is connected to the light source 9 and the other one to the detector 11. The end 12 of the lightguide is placed flush against the exterior 13 of the wall of the container, transmitting excitation radiation towards the optodes 3a, 3b and 3c through the transparent wall of the container, while receiving the optical signal, e.g. the fluorescence radiation emitted by the optodes.

The use of suitable filtering means 31, for instance, a filter disk, in front of the detector 11 will ensure that the signals are assigned to their corresponding optodes 3a, 3b, 3c.

Via a line 14 the detector signals are transmitted to an evaluation unit 15, in which detector signals change over time, e.g. the $CO_2$ content is determined and the status of the sample is indicated via a display 16.

The conditions in the container necessary for the metabolic processes are maintained by means of the unit 17, which is mainly responsible for proper temperature control of the sample and is connected with the evaluation unit 15 via a control lead 18.

Instead of the unit 17, an air heating element may be used for sample temperature control in the variant of FIG. 1 and all subsequent variants.

Figure 2A:
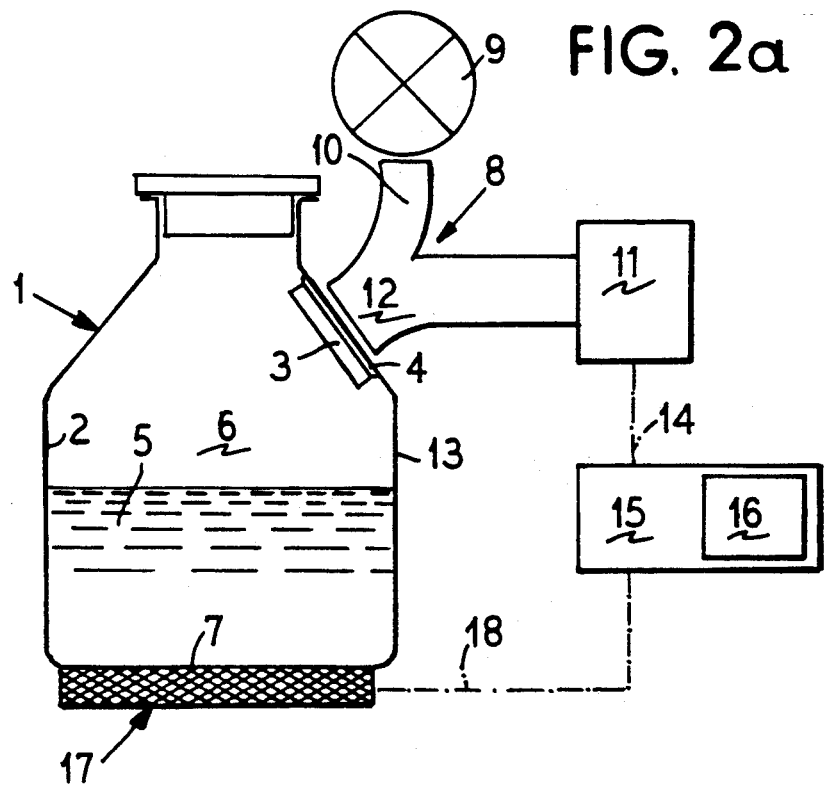

The variant shown in FIG. 2a differs from that in FIG. 1 only by the fact that the optode 3 is located in the gas space 6 of the container 1 and that gaseous metabolites may be measured only. In this case temperature control is performed via the bottom 7 of the container 1. In a variant according to FIG. 2b the optode 3, or optodes 3a, 3b, may be attached to a stopper 1' sealing the container 1. The lightguide 10 either may go through this stopper, or it may be placed on the outside of a transparent stopper 1', as is shown in FIG. 2b.

In another variant presented in FIG. 3 the optode 3 is attached to the tip of a probe 19 receiving the end of the two-armed light waveguide 10. The probe 19 is introduced into the container 1 through the opening 21 sealed by a septum 20, and may be axially shifted along the double-headed arrow 22, permitting measurements to be taken both in the gas space 6 and in the culture medium 5.

In the variant shown in FIG. 4 the optode 3, which is used, for instance, for measuring $O_2$ and $CO_2$, is not located in the container 1, but is placed in a sampling vessel 23 instead. In order to introduce the sample into the culture bottle the septum 20 of the container 1 is punctured with the hollow needle 24 of the sampling vessel 23, permitting the sample to enter the culture medium. Via the hollow needle 24 a gas exchange will take place between the gas space 6 and the interior 25 of the sampling vessel 23, such that the change in the concentration of $CO_2$ and $O_2$ may be determined with the use of the excitation and detection assembly 8 not shown here in detail.

Figure 5:
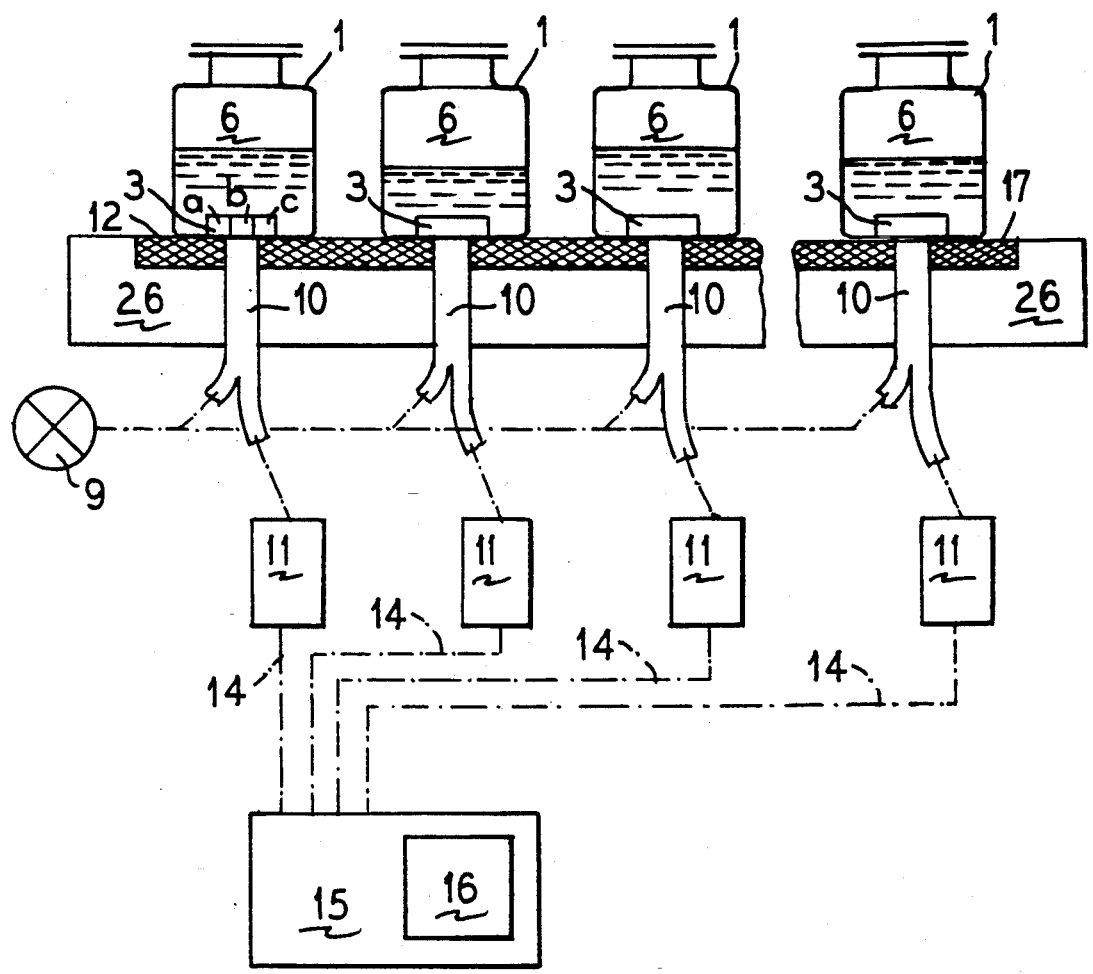

A particularly favorable variant is shown in FIG. 5, comprising a device 26 configured as a temperature-controlled supporting rack, which will hold several containers 1 at the same time. The containers are inserted in labelled positions and are arranged in several rows, permitting temperature control and continuous monitoring of up to 600 containers simultaneously. Each container is assigned a two-armed light waveguide 10 located in the supporting rack 26 and providing the optodes 3a to 3c at the bottom of each container 1 with excitation radiation. The corresponding optical signals are delivered to the individual detectors 11 connected to the evaluation unit 15 via lines 14. The individual readings delivered to the evaluation unit 15 are accompanied by suitable position identification signals, such that the individual values may directly be assigned to the corresponding sample.

Figure 6:
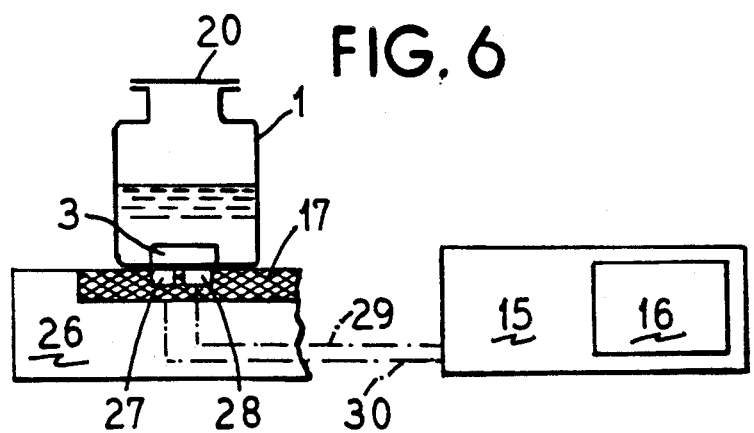

A variant as presented in FIG. 6 provides that each individual container 1 be connected with a LED 27 located in the supporting rack 26 and with a photodiode 28, possibly in conjunction with filter elements. In this way a most compact device is obtained which is characterized by the total absence of movable parts.

Figure 7:
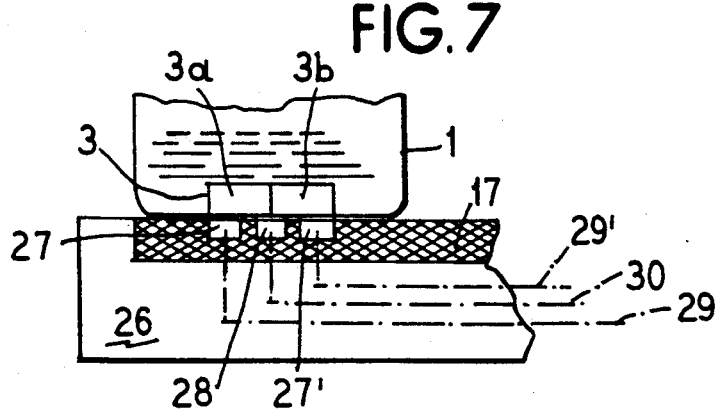

FIG. 7 gives a variant according to FIG. 6, which contains two optodes, 3a and 3b, combined into a sensor (e.g. a bisensor for simultaneous measurement of $O_2$ concentration and pH). The optodes are excited via differing LED's 27 and 27', whose emission radiation is received by a common photodiode 28. The corresponding electrical leads 29, 29', 30 lead to the evaluation unit not shown here. By means of known optical or electronic equipment, the signals of the two optodes may be separated. Other variants with only one LED for excitation and several photodiodes for signal detection are within the scope of the invention.

Figure 8:
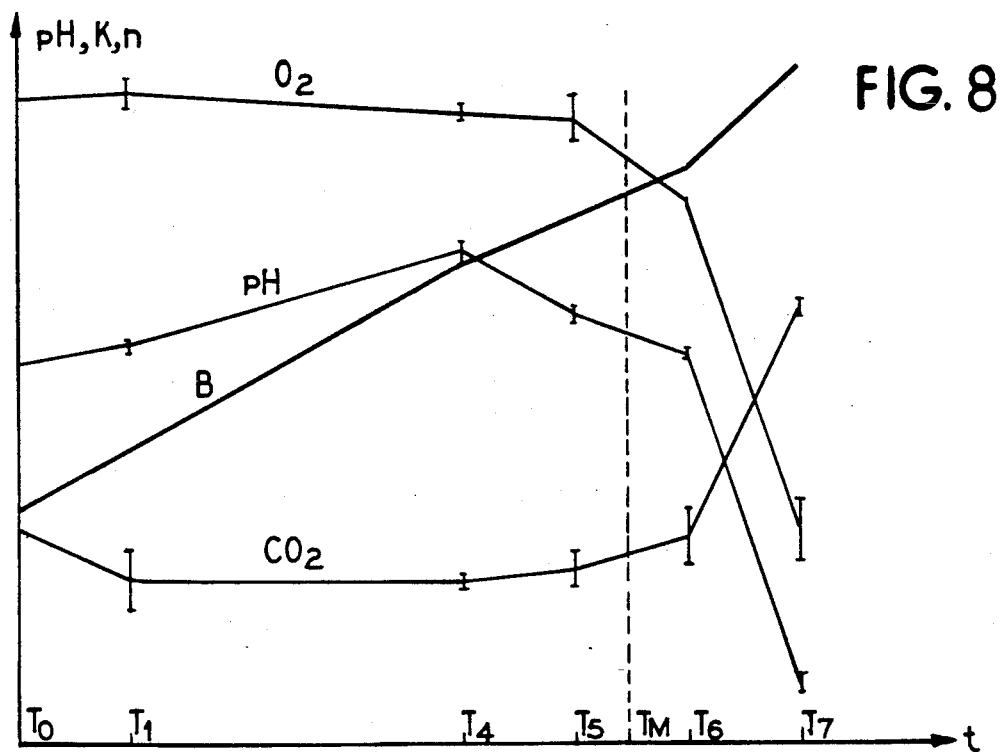
Figure 9:
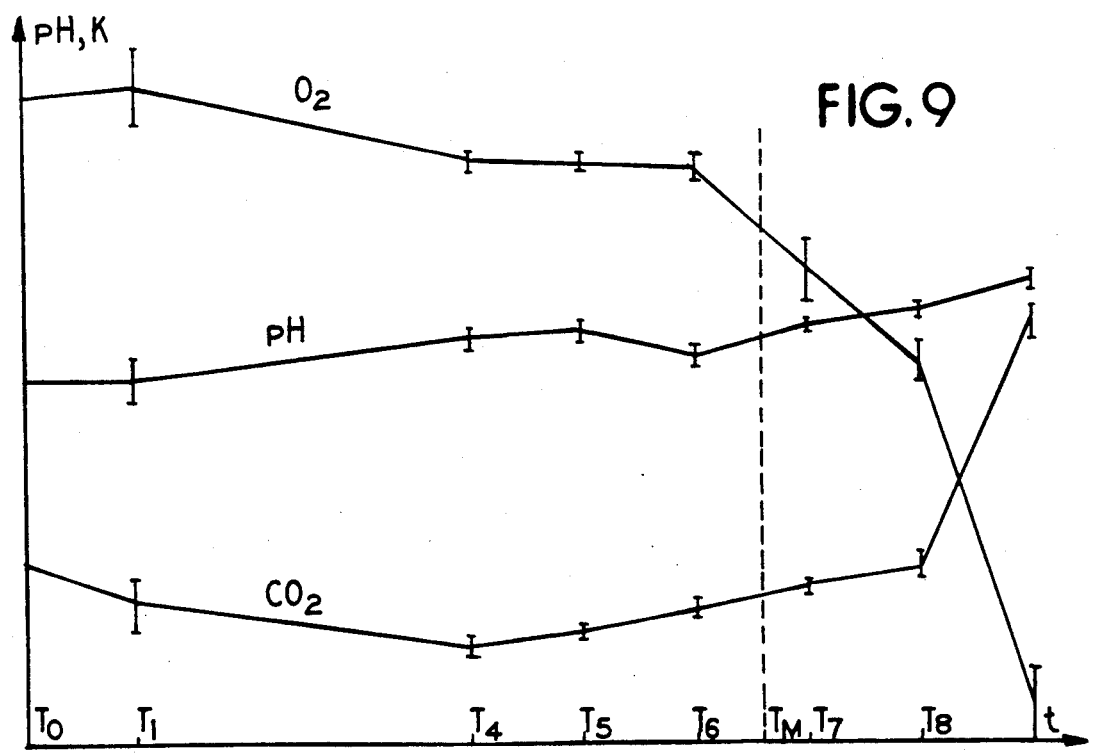

In the diagrams shown in FIGS. 8 and 9 the time t, or rather, individual points in time $T_0$ to $T_8$, are plotted on the abscissa, while the pH value, the concentration K (or the partial pressure of $O_2$ and $CO_2$) and the number of bacteria or organisms per unit volume (logarithmic scale) are plotted on the ordinate.

FIG. 8 shows the change over time of the parameters $O_2$, $CO_2$ and pH, using a sample containing *Staphylococcus aureus*. Between $T_5$ and $T_6$ the concentration of $CO_2$ is characterized by a significant increase indicating a positive sample, whereupon the $O_2$ concentration and pH are determined at the point in time $T_M$. The sharp decrease in both $O_2$ concentration and pH indicate Gram positive *Staphylococcus aureus*.

As opposed to FIG. 8, the pH value in FIG. 9 remains largely unchanged, which indicates the presence of Pseudomonas species (cf. the above table). In this instance a sample with *Pseudomonas aeruginosa* was used.

Figure 10:
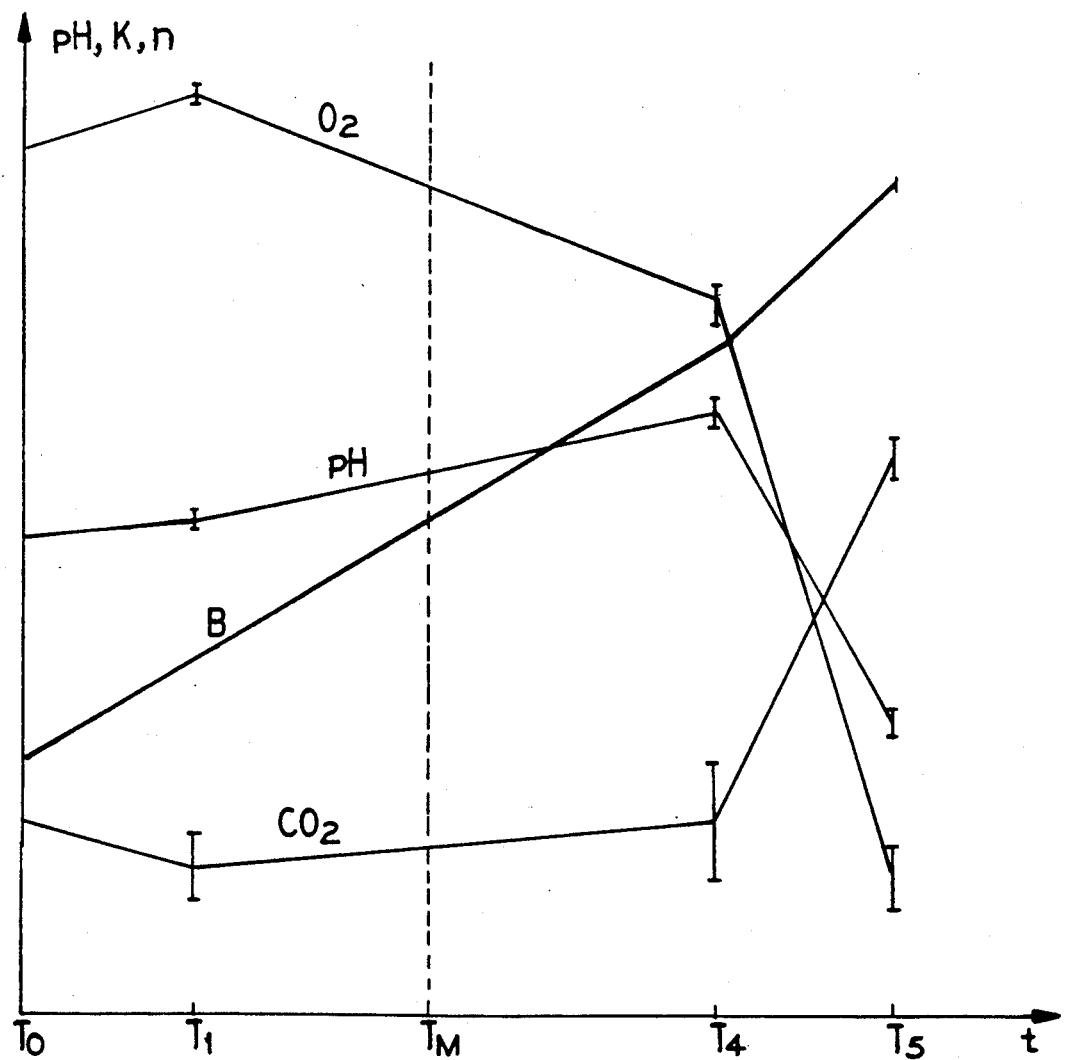

The values given in FIG. 10 are taken from a sample containing Enterobacteria (*E. coli*).

The method and device described in this paper are well suited for detecting biological activities in samples, for instance, of germs in blood, bacteriemia, septicemia or pyemia, but also of algae, bacteria or other germs.

The continuous, non-invasive monitoring of specimens helps to obtain fully automated incubation and measuring processes for a large number of samples. Positive cultures are quickly identified and erroneous negative findings are avoided.

We claim:

1. A method for detecting biological activities in a microorganism-containing specimen which a sample of the specimen and a culture medium are disposed in a sealable container and are exposed to conditions enabling metabolic processes to take place as a result of the presence of said microorganisms in the sample such that the concentration of initial substances in said sample is lowered and the concentration of metabolic products is raised, the improvement therein comprising the steps of:

continually measuring the change in concentration of one first substance generated by metabolic processes in the sample using a first optode disposed in said container;

simultaneously measuring the change in concentration of a second substance generated by metabolic processes in the identical said sample using a second optode disposed in the same container whereby changes in said sample will simultaneously affect both said first and second substances;

said measuring including simultaneously generating a first output signal with said first optode and a second output signal with said second optode, said first and second output signals being respectively indicative of said changes in said concentrations of said first and second substances;

and monitoring the output signals over time and identifying a type of microorganism contained in said specimen from said changes in concentration of the substances being measured simultaneously from the same sample.

2. The method of claim 1 comprising the additional step of:

obtaining said first and second output signals externally of the container from said first and second optodes.

3. The method of claim 1 further comprising:

measuring the concentrations of at least two substances selected from the group consisting of $CO_2$, $O_2$, $H^+(pH)$, $NH_4^+$, $H_2S$ and $H_2$; and monitoring an indicator medium contained within the optode structure for a change of behavior of at least one behavior selected from the group consisting of luminescence, absorption, and reflectance.

4. The method of claim 2 further comprising:

measuring the concentrations of at least two substances selected from the group consisting of $CO_2$, $O_2$, $H^+(pH)$, $NH_4^+$, $H_2S$ and $H_2$; and monitoring an indicator medium contained within the optode structure for change of luminescence decay time of the emitted luminescent radiation corresponding to change of substance concentration.

5. The method of claim 1, wherein the step of continually measuring further comprises:

monitoring the changes in the $CO_2$ concentration as a first substance for a rise of 0.1–10% above a predetermined minimum value;

determining changes in the $O_2$ concentration as a second substance;

and measuring $H^+(pH)$ as a third substance.

6. The method of claim 1 further comprising:

monitoring the $O_2$ concentration as a first substance and the pH as a second substance for slight decreases as an indication of the presence of enterobacteria or *Staphylococcus epidermidis*.

7. The method of claim 1 further comprising:

monitoring one of said substances for Gram staining, where negative Gram staining indicates the presence of enterobacteriae, and positive Gram staining indicates the presence of *Staphylococcus epidermidis*.

8. The method of claim 1 further comprising:

monitoring the $O_2$ concentration as said first substance for a sharp decrease;

and monitoring a stable $H^+(pH)$ as a second substance as an indication of the presence of Pseudomonas species.

9. The method of claim 1 further comprising:

monitoring the $O_2$ concentration as a first substance for a sharp decrease and a slight decrease in $H^+(pH)$ as a second substance as an indication of the presence of Acinetobacter species.

10. The method of claim 1 further comprising:

monitoring the $O_2$ concentration as a first substance for no change and $H^+(pH)$ as a second substance for a slight decrease as an indication of the presence of Bacteroid species.

11. The method of claim 1 further comprising:

monitoring both the $O_2$ concentration as a first substance and $H^+(pH)$ as a second substance for a sharp decrease indicating the presence of *Staphylococcus aureus* or *Streptococcus faecalis*.

12. The method of claim 1 further comprising:

monitoring the $O_2$ concentration as a first substance for a slight decrease and $H^+$ (pH) as a second substance for a sharp decrease as an indication of the presence of *Streptococcus pyogenes*, *Streptococcus pneuoniae* or *Candida albicans*.

13. The method of claim 1 further comprising:

monitoring the $O_2$ concentration as a first substance for no change and $H^+(pH)$ as a second substance for a sharp decrease as an indication of the presence of *Clostridium perfringens*.

14. The method of claim 1, wherein the step of continually measuring further comprises:

monitoring the changes in the $O_2$ concentration as a first substance for a drop of 0.1–10% below a predetermined maximum value and determining changes in the $CO_2$ concentration as a second substance and $H^+(pH)$ as a third substance.

15. The method of claim 1 further comprising:

monitoring the $O_2$ concentration as a first substance and $H^+(pH)$ as a second substance for respective slight decreases as an indication of the presence of enterobacteria or *Staphylococcus epidermidis*.

* * * * *